(12) United States Patent
Hu et al.

(10) Patent No.: US 7,820,653 B2
(45) Date of Patent: Oct. 26, 2010

(54) PHOTOSENSING SOLUBLE ORGANIC SEMICONDUCTOR MATERIAL

(75) Inventors: Tarng-Shiang Hu, Hsinchu (TW);
Hsiang-Yuan Cheng, Taipei (TW);
Jia-Chong Ho, Hsinchu County (TW);
Tzu-Wei Lee, Chiayi (TW); Ming-Chou Chen, Hsinchu (TW); Jen-Shyang Ni, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 879 days.

(21) Appl. No.: 11/552,990

(22) Filed: Oct. 26, 2006

(65) Prior Publication Data
US 2007/0262298 A1 Nov. 15, 2007

(30) Foreign Application Priority Data
May 9, 2006 (TW) .............................. 95116329 A

(51) Int. Cl.
*A61K 31/5415* (2006.01)
(52) U.S. Cl. ...................................... 514/226.5; 544/14
(58) Field of Classification Search ..................... 544/14
See application file for complete search history.

(56) References Cited

U.S. PATENT DOCUMENTS

2003/0144562 A1   7/2003   Afzali-Ardakani et al.

OTHER PUBLICATIONS

K. P. Weidkamp et al., "A Photopatternable Pentacene Precursor for Use in Organic Thin-Film Transistors," Journal of the American Chemical Society, 2004, vol. 126 No. 40, Sep. 16, 2004, pp. 12740-12741.
A. Afzali et al., "High-Performance, Solution-Processed Organic Thin Film Transistors from a Novel Pentacene Precursor," 2002 American Chemical Society, 124, pp. 8812-8813.

*Primary Examiner*—James O Wilson
*Assistant Examiner*—Brian McDowell
(74) *Attorney, Agent, or Firm*—Jianq Chyun IP Office

(57) ABSTRACT

A photosensing soluble organic semiconductor material is disclosed, which includes a Diels-Alder adduct which is a polycyclic aromatic compound with a dienophile. The polycyclic aromatic compound is pentacene. And the dienophile is represented by the formula of $O=S=N-R^1$, wherein $R^1$ is $SO_2R^2$, $SO_3R^2$, $SO_2^-$, or $SO_3^-$; and wherein $R^2$ is selected from the group consisting of alkyl, alkoxy, acyl, aryl, aralkyl, chloroalkyl, fluoroalkyl, and substituted aryl with 1-12 carbon atoms. The structural formula of the adduct is as follows:

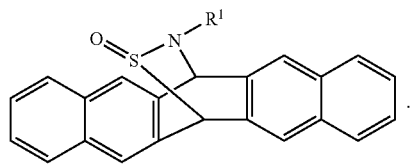

6 Claims, No Drawings

PHOTOSENSING SOLUBLE ORGANIC SEMICONDUCTOR MATERIAL

CROSS-REFERENCE TO RELATED APPLICATION

This application claims the priority benefit of Taiwan application serial no. 95116329, filed on May 9, 2006. All disclosure of the Taiwan application is incorporated herein by reference.

BACKGROUND OF THE INVENTION

1. Field of Invention

The present invention relates to a semiconductor material applied in an organic thin film transistor (OTFT). More particularly, the present invention relates to a photosensing soluble organic semiconductor material.

2. Description of Related Art

The greatest difference between an organic thin film transistor and a Metal Oxide Semiconductor (MOS) transistor is that an organic semiconductor material is utilized in the organic thin film transistor to replace an inorganic semiconductor material used in the MOS transistor. Generally, the organic thin film transistor is a transistor made from an organic conjugated polymer or oligomer material. Compared with the traditional inorganic transistor, the organic thin film transistor can be prepared at low temperature, thus a lighter, thinner, and cheaper plastics can be employed to substitute the glass as a substrate.

Moreover, the process of an organic thin film transistor is simple, including directly patterning an organic thin film with a printing technique, which can reduce the number of the masks and decrease the usage cost of the vacuum vapor deposition apparatus, and is highly compatible with subsequent roll to roll continuous process because of being suitable for plastics substrates, thus greatly reducing the manufacturing cost.

SUMMARY OF THE INVENTION

Accordingly, the present invention is directed to provide a photosensing soluble organic semiconductor material, so that the organic thin film transistor (OTFT) may have more opportunities to be applied in electronic products with low cost and large areas.

Another object of the present invention is to provide a photosensing soluble organic semiconductor material, which can reduce the number of the masks and decrease the usage cost of the vacuum vapor deposition apparatus, i.e., which can be applied in the manufacture of electronic products with low cost and large areas.

The present invention proposes a photosensing soluble organic semiconductor material including an adduct obtained from the Diels-Alder reaction, which adduct is a polycyclic aromatic compound with a dienophile. The polycyclic aromatic compound is selected from the group consisting of oligothiophene, perylene, benzo[ghi]perylene, coronene, and polyacene. And the dienophile is represented by the formula of O=S=N—$R^1$, wherein $R^1$ is $SO_2R^2$ or $SO_3R^2$, and wherein $R^2$ is selected from the group consisting of alkyl, alkoxy, acyl, aryl, aralkyl, chloroalkyl, fluoroalkyl, and substituted aryl of 1-12 carbon atoms. The substituted aryl has a substituent selected from the group consisting of —F, —Cl, —Br, —$NO_2$, —$PO_3H$, —$SO_3H$, trialkylsilyl, and acyl.

According to the photosensing soluble organic semiconductor material described in one embodiment of the present invention, the structural formula of the adduct is as follows:

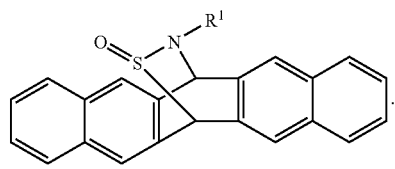

According to the photosensing soluble organic semiconductor material described in one embodiment of the present invention, the structural formula of the adduct is as follows:

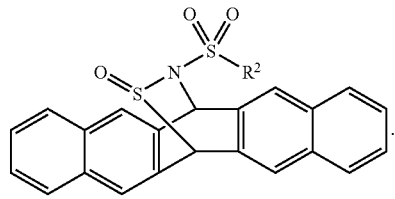

According to the photosensing soluble organic semiconductor material described in one embodiment of the present invention, the structural formula of the adduct is as follows:

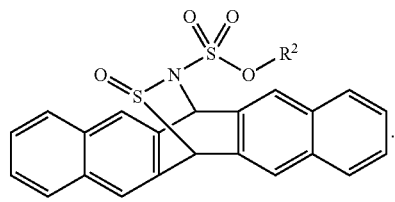

According to the photosensing soluble organic semiconductor material described in one embodiment of the present invention, the polycyclic aromatic compound includes a polyacene, and the structural formula of the polyacene is as follows:

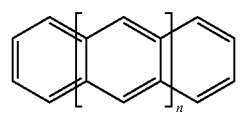

wherein n is at least 2.

According to the photosensing soluble organic semiconductor material described in one embodiment of the present invention, the polyacene may be pentacene.

The present invention further proposes a photosensing soluble organic semiconductor material including an adduct obtained from the Diels-Alder reaction, which adduct is a polycyclic aromatic compound with a dienophile, wherein the polycyclic aromatic compound is selected from the group consisting of oligothiophene, perylene, benzo[ghi]perylene, coronene, and polyacene. And the dienophile is represented by the formula of O=S=N—$R^1$, wherein $R^1$ is $SO_2^-$ or $SO_3^-$.

According to the photosensing soluble organic semiconductor material described in another embodiment of the present invention, the structural formula of the adduct is as follows:

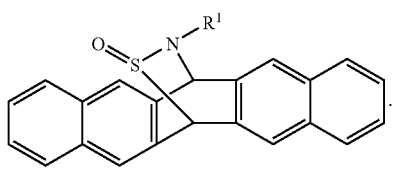

According to the photosensing soluble organic semiconductor material described in another embodiment of the present invention, the structural formula of the adduct is as follows:

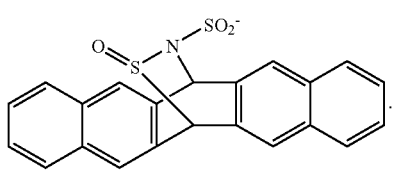

According to the photosensing soluble organic semiconductor material described in another embodiment of the present invention, the structural formula of the adduct is as follows:

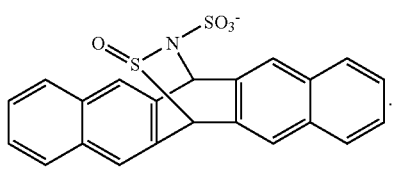

According to the photosensing soluble organic semiconductor material described in another embodiment of the present invention, the polycyclic aromatic compound includes a polyacene, and the structural formula of the polyacene is as follows:

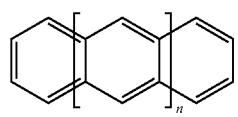

wherein n is at least 2.

According to the photosensing soluble organic semiconductor material described in another embodiment of the present invention, the polyacene is, for example, pentacene.

The present invention enables the organic thin film transistor (OTFT) to be applied in electronic products with low cost and large areas because a micromolecular organic semiconductor material is combined with different functional groups to form a photosensing soluble organic semiconductor material. Moreover, the photosensing soluble organic semiconductor material of the present invention may be formed to a patterned thin film directly by a printing technique, so the number of the masks can be reduced and the usage cost of the vacuum vapor deposition apparatus can be decreased. Additionally, the present invention is highly compatible with subsequent continuous process and is greatly favorable for decreasing the manufacturing cost because it is suitable for plastic substrates, therefore, it can be used in the manufacture of electronic products with low cost and large areas.

In order to make the aforementioned and other objects, features and advantages of the present invention comprehensible, preferred embodiments are exemplified in detail below.

DESCRIPTION OF EMBODIMENTS

The present invention relates to a photosensing soluble organic semiconductor material, mainly by combining a micromolecular organic semiconductor material with different functional groups to form the photosensing soluble organic semiconductor material.

First Embodiment

The photosensing soluble organic semiconductor material in this embodiment includes an adduct obtained from the Diels-Alder reaction, which is also known as the diene addition reaction. And the adduct is a polycyclic aromatic compound with a dienophile.

In the embodiment, the polycyclic aromatic compound is selected from the group consisting of oligothiophene, perylene, benzo[ghi]perylene, coronene, and polyacene.

In the embodiment, the dienophile is represented by the formula of O=S=N—$R^1$, wherein $R^1$ is $SO_2R^2$ or $SO_3R^2$, and wherein $R^2$ is selected from the group consisting of alkyl, alkoxy, acyl, aryl, aralkyl, chloroalkyl, fluoroalkyl, and substituted aryl of 1-12 carbon atoms. The substituted aryl has a substituent selected from the group consisting of —F, —Cl, —Br, —$NO_2$, —$PO_3H$, —$SO_3H$, trialkylsilyl, and acyl.

An example is proposed to illustrate the first embodiment in detail, but the present invention is not limited to the semiconductor material described in this example.

Example 1

When the polycyclic aromatic compound of the photosensing soluble organic semiconductor material in the first embodiment is the polyacene of the following structural formula (1):

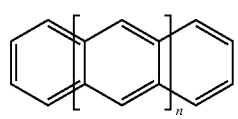

(1)

wherein n is at least 2, and the polyacene is pentacene (i.e., n is 3), the adduct of the first embodiment is of the following structural formula (2):

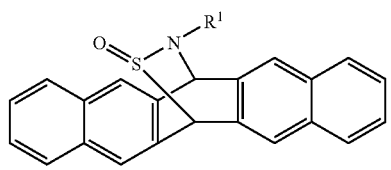

(2)

As $R^1$ is $SO_2R^2$ or $SO_3R^2$, the adduct in example 1 may be of either the following structural formula (3) or structural formula (4):

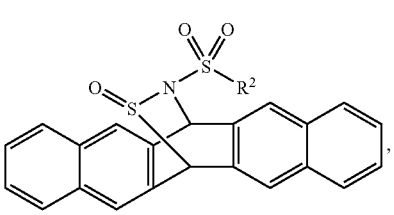

(3)

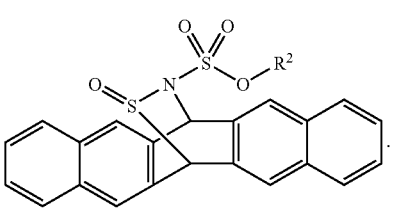

(4)

The photosensing soluble organic semiconductor material of the structural formula (3) or structural formula (4) is prepared mainly by combining a micromolecularorganic semiconductor material like polycyclic aromatic compound with the dienophile described in the first embodiment in a Diels-Alder reaction.

For example, the dienophile such as N-sulfinyl-R-sulfonamide or N-sulfinyl-R-amidosulfate can be reacted with a pentacene in a Diels-Alder reaction, the reaction equation of which is as follows:

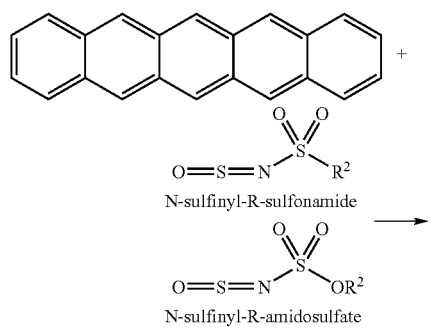

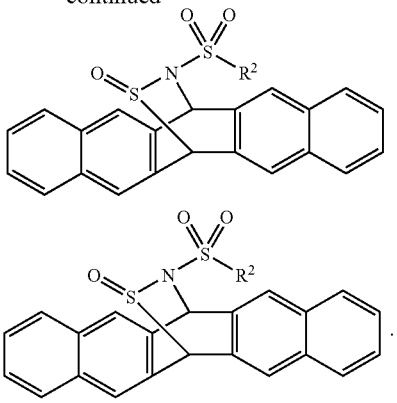

The photosensing soluble organic semiconductor material which acts as the precursor of the organic semiconductor material can be coated onto a substrate directly with the methods of inkjet printing, micro contact printing, nanoimprinting, spin-coating-yellow photolithography, etc. Thereafter, the precursor may be reduced to a micromolecular organic semiconductor by the control of the process, for example, the steps of heating, baking or lighting, etc., so as to achieve the preparation of an organic semiconductor with a solution process. The following is the reaction equation of the reduction of the structural formula (3) of example 1 to a pentacene through the steps of heating, baking or lighting, etc.:

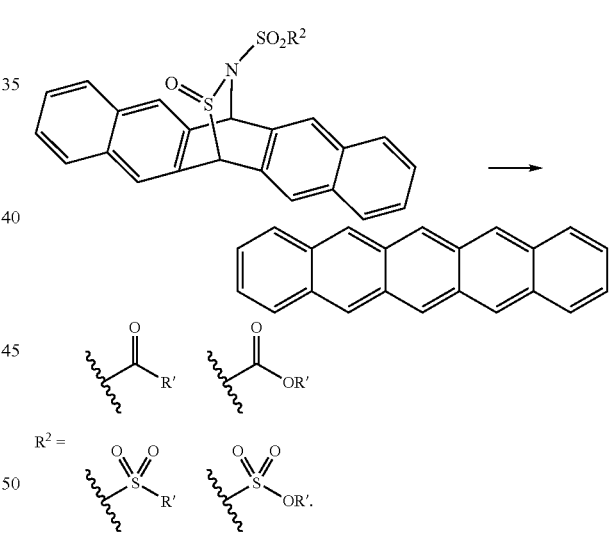

Second Embodiment

The greatest difference between the photosensing soluble organic semiconductor material in the second embodiment and that in the first embodiment is that $R^1$ in the formula of dienophile: $O\!=\!S\!=\!N\!-\!R^1$, and $R^1$ is $SO_2^-$ or $SO_3^-$. The polycyclic aromatic compound of the photosensing soluble organic semiconductor material is selected from the group consisting of oligothiophene, perylene, benzo[ghi]perylene, coronene, and polyacene.

An example is proposed to illustrate the second embodiment in detail, but the present invention is not limited to the semiconductor material described in this example.

Example 2

When the polycyclic aromatic compound of the photosensing soluble organic semiconductor material in the second embodiment is the polyacene of the following structural formula (1):

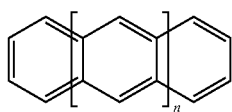

(1)

wherein n is at least 2, and the polyacene used in this example 2 is pentacene, the adduct of the second embodiment is of either the following structural formula (5) or structural formula (6):

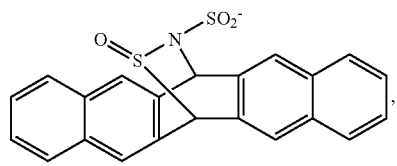

(5)

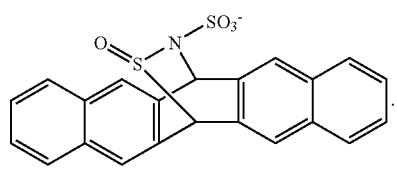

(6)

Furthermore, the preparation of the photosensing soluble organic semiconductor material of the structural formula (5) or structural formula (6) is also performed by combining a polycyclic aromatic compound with the dienophile described in the second embodiment in a Diels-Alder reaction, the reaction equation of which is as follows:

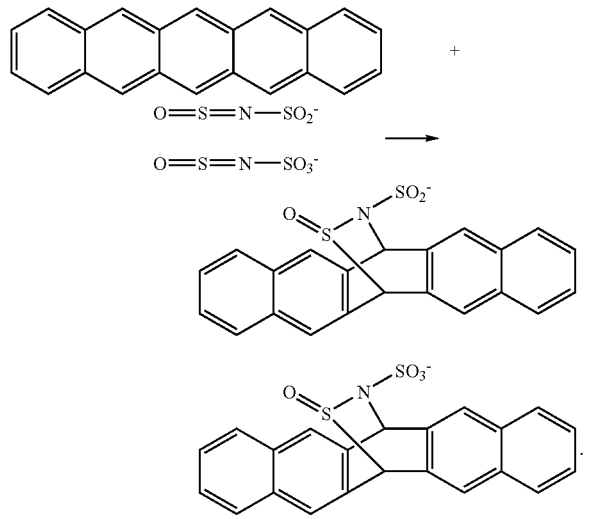

Furthermore, the photosensing soluble organic semiconductor material can be coated onto a substrate directly with the methods of inkjet printing, micro contact printing, nanoimprinting, spin-coating-yellow photolithography, etc. Thereafter, it may be reduced to a micromolecular organic semiconductor by the control of the process, for example, the steps of heating, baking or lighting, etc., so as to achieve the preparation of an organic semiconductor with a solution process.

In conclusion, the present invention is characterized by combining a micromolecular organic semiconductor material with different functional groups to form a photosensing soluble organic semiconductor material, thus enabling the organic thin film transistor (OTFT) to be applied in electronic products with low cost and large areas. Moreover, the material of the present invention may be formed to a patterned thin film directly by employing a print technique, so the number of the masks can be reduced while the usage cost of the vacuum vapor deposition apparatus can be decreased. Moreover, the present invention is highly compatible with subsequent continuous process and is greatly favorable for decreasing the manufacturing cost because it is suitable for flexible plastic substrates with low cost, therefore, it can be used in the manufacture of the electronic products with low cost and large areas.

Although the present invention has been disclosed in the preferred embodiments as above, it is not intended to limit the present invention. Various variations and modifications can be made by any of those skilled in the art without deviating from the spirit and scope of the present invention. Therefore, the scope of the present invention depends on that defined in the appended claims.

What is claimed is:

1. A photosensing soluble organic semiconductor material, comprising an adduct obtained from the Diels-Alder reaction, wherein the structural formula of the adduct is as follows:

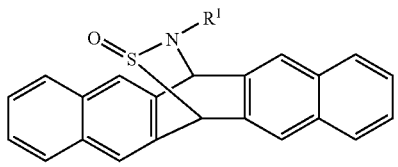

wherein $R^1$ is $SO_2R^2$ or $SO_3R^2$, and wherein $R^2$ is selected from the group consisting of alkyl, alkoxy, aryl, aralkyl, chloroalkyl, fluoroalkyl, and a substituted aryl with 1-12 carbon atoms, and the substituted aryl has a substituent selected from the group consisting of —F, —Cl, —Br, —$NO_2$, —$PO_3H$, —$SO_3H$, and trialkylsilyl.

2. The photosensing soluble organic semiconductor material as claimed in claim 1, wherein the structural formula of the adduct is as follows:

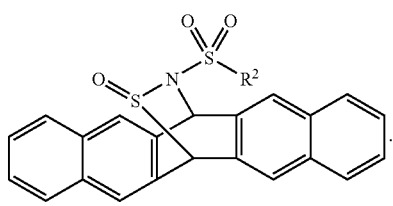

3. The photosensing soluble organic semiconductor material as claimed in claim 1, wherein the structural formula of the adduct is as follows:

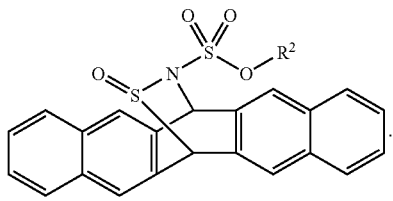

4. A photosensing soluble organic semiconductor material, comprising an adduct obtained from the Diels-Alder reaction, wherein the structural formula of the adduct is as follows:

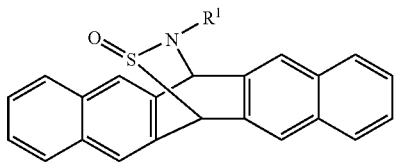

wherein $R^1$ is $SO_2^-$ or $SO_3^-$.

5. The photosensing soluble organic semiconductor material as claimed in claim 4, wherein the structural formula of the adduct is as follows:

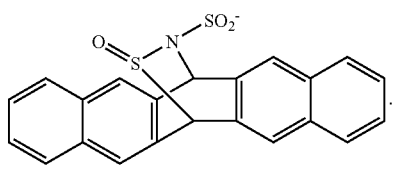

6. The photosensing soluble organic semiconductor material as claimed in claim 4, wherein the structural formula of the adduct is as follows:

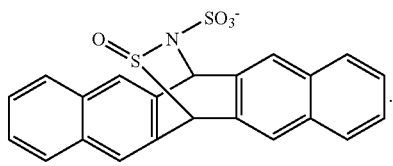

* * * * *